United States Patent
Rheault et al.

(10) Patent No.: US 12,130,162 B2
(45) Date of Patent: Oct. 29, 2024

(54) OPTICAL BUBBLE SENSOR

(71) Applicant: Strain Measurement Devices, Inc., Wallingford, CT (US)

(72) Inventors: Kristin N. Rheault, Glastonbury, CT (US); Samuel A. Matus, Berlin, CT (US); Frederick E. Jackson, Branford, CT (US)

(73) Assignee: STRAIN MEASUREMENT DEVICES, INC., Wallingford, CT (US)

( * ) Notice: Subject to any disclaimer, the term of this patent is extended or adjusted under 35 U.S.C. 154(b) by 176 days.

(21) Appl. No.: 17/861,507

(22) Filed: Jul. 11, 2022

(65) Prior Publication Data
US 2023/0018969 A1    Jan. 19, 2023

Related U.S. Application Data

(60) Provisional application No. 63/220,818, filed on Jul. 12, 2022.

(51) Int. Cl.
*G01F 1/74*  (2006.01)
*G01F 1/7086*  (2022.01)

(52) U.S. Cl.
CPC .............. *G01F 1/74* (2013.01); *G01F 1/7086* (2013.01)

(58) Field of Classification Search
None
See application file for complete search history.

(56) References Cited

U.S. PATENT DOCUMENTS

| | | | |
|---|---|---|---|
| 7,998,115 B2 * | 8/2011 | Bedingfield | A61M 1/155 417/477.2 |
| 10,895,843 B2 * | 1/2021 | Hong | G03H 1/0443 |
| 10,996,091 B2 * | 5/2021 | Meribout | G01F 1/712 |
| 2009/0319204 A1 * | 12/2009 | Brown | G01F 1/712 702/47 |
| 2022/0008637 A1 * | 1/2022 | Kumar | G06T 7/62 |

* cited by examiner

*Primary Examiner* — Peter J Macchiarolo
*Assistant Examiner* — Jermaine L Jenkins
(74) *Attorney, Agent, or Firm* — CANTOR COLBURN LLP

(57) ABSTRACT

An optical sensor includes: a sensor portion, having a transmitter and at least one receiver, configured to couple to a wettable component having a fluid flow channel, wherein the transmitter is disposed to emit a light that travels from the sensor portion to the wettable component where a majority of the light is directed towards the fluid flow channel at an angle between a first critical angle and a second critical angle; wherein with liquid filling the fluid flow channel, the majority of the light refracts at a liquid interface and travels through the entirety of the fluid flow channel; wherein with gas in the fluid flow channel, the majority of the light reflects at a gas interface and does not travel through the entirety of the fluid flow channel; wherein the amount of the light refracted and/or reflected and received by the at least one receiver, is used to determine if there is liquid or gas in the fluid flow channel.

18 Claims, 10 Drawing Sheets

OPTICAL BUBBLE SENSOR

CROSS REFERENCE TO RELATED APPLICATIONS

This application claims the benefit of U.S. Provisional Application Ser. No. 63/220,818, filed Jul. 12, 2022, which is incorporated herein by reference in its entirety.

BACKGROUND

The present disclosure relates generally to an optical bubble sensor, and particularly to an optical bubble sensor having refractive surfaces, reflective surfaces, or both refractive and reflective surfaces.

A bubble sensor (also known as an air-in-line sensor, or air detector) is a device used in many fluid management applications to detect the presence of air bubbles, or gas bubbles generally, in a liquid flow channel. Conversely it can be used to detect the presence of liquid in a flow channel that should typically remain dry. Bubble sensors are used in many industries and applications, including in medical fluid management to prevent the injection of air bubbles into a patient's circulatory system.

There currently exist two common methods for detecting gas bubbles in liquid-filled flow channels: ultrasonic bubble detectors; and, attenuative optical bubble sensors (commonly referred to as "optical bubble sensors"). Attenuative optical bubble sensors work by sending light (typically visible or infrared wavelength) into one side of a flow channel and through the fluid to measure the amount of light received on the other side of the channel. Depending on the optical properties of the fluid, such as the absorption of light at that wavelength, the amount of light received may increase or decrease relative to the presence of gas. This type of sensor works well in some applications, however, it often requires frequent calibration and can be difficult to calibrate in applications that use multiple liquids with varying optical absorption properties. Ultrasonic bubble sensors are the most used type and detect bubbles reliably in applications for which they are well suited. However, because materials must be in intimate contact, and with no air gaps, in order for ultrasound waves to pass between them, ultrasonic sensors are best suited for flow channels made from compliant materials that ultrasonically couple well to a sensor, such as round soft or semi-soft plastic or rubber tubing.

In many cases where bubble sensors are used, such as medical fluid management devices, the fluid must remain sterile. Therefore, there are two components: a sterile disposable component set that contacts the fluid; and, a durable hardware component set that includes pumps, valves, sensors, electronics, etc. The need for sterility necessitates all sensing to be done non-invasively, i.e. the sensors cannot contact the fluid. In many cases, the flow channel of the disposable component set is a round compliant tube that works well with existing ultrasonic bubble sensing technology. However, in some cases, the channel that liquid flows through is a custom-designed rigid flow channel to facilitate proper installation of the disposable component set by the end-user. This flow channel is commonly referred to as a "cartridge". Cartridges allow the disposable component set to be installed into the device in one simple motion, which mitigates the need to ensure that a piece of tubing gets properly interfaced with every sensor, valve, and pump, on the device. The installation process is particularly important in complex systems with multiple fluid streams such as dialysis machines.

The current state of bubble sensing technology leaves a gap in the ability to reliably detect bubbles in rigid disposable cartridges without the use of complex and expensive loading and coupling mechanisms. As such, there is a need in the art of bubble sensing to overcome these existing deficiencies.

BRIEF SUMMARY

An embodiment includes an optical bubble sensor as defined by the appended independent claim(s). Further advantageous modifications of the optical bubble sensor are defined by the appended dependent claims.

In an embodiment, an optical sensor includes: a sensor portion having an optical transmitter and at least one optical receiver, the sensor portion configured to couple to a wettable component at least one coupling interface, the wettable component having a housing with a fluid flow channel, the at least one coupling interface having of at least one coupling surface on the wettable component and at least one coupling surface on the sensor portion, the at least one optical receiver having a refractive receiver, a reflective receiver, or both the refractive receiver and the reflective receiver, wherein the optical transmitter is disposed and configured to emit an incident light; wherein the optical transmitter and the at least one coupling interface are disposed such that the incident light emitted from the optical transmitter, when active, travels from the sensor portion to the wettable component where a majority of the incident light is directed towards the fluid flow channel at an angle between a first critical angle and a second critical angle, the first critical angle being defined relative to the wettable component and a liquid, and the second critical angle being defined relative to the wettable component and a gas; wherein in the presence of a liquid substantially filling the fluid flow channel of the wettable component, the majority of the incident light refracts at a liquid interface between the fluid flow channel and the liquid and travels through the entirety of the fluid flow channel; wherein in the presence of a gas in the fluid flow channel of the wettable component, the majority of the incident light reflects at a gas interface between the fluid flow channel, or the liquid in the fluid flow channel, and the gas, and does not travel through the entirety of the fluid flow channel; wherein at least one of: the majority of the incident light refracted; and, the majority of the incident light reflected, travels from the wettable component to the sensor portion and is received by the at least one optical receiver; wherein the at least one optical receiver is disposed such that it intersects at least one of: the majority of incident light refracted; and, the majority of the incident light reflected; and, wherein at least one of: the amount of the majority of the incident light refracted and received by the at least one optical receiver; and, the amount of the majority of the incident light reflected and received by the at least one optical receiver, is used to determine if there is liquid or gas in the fluid flow channel.

The above features and advantages and other features and advantages of the invention are readily apparent from the following detailed description of the invention when taken in connection with the accompanying drawings.

BRIEF DESCRIPTION OF THE DRAWINGS

Referring to the exemplary non-limiting drawings wherein like elements are numbered alike in the accompanying Figures.

Figure 1A:
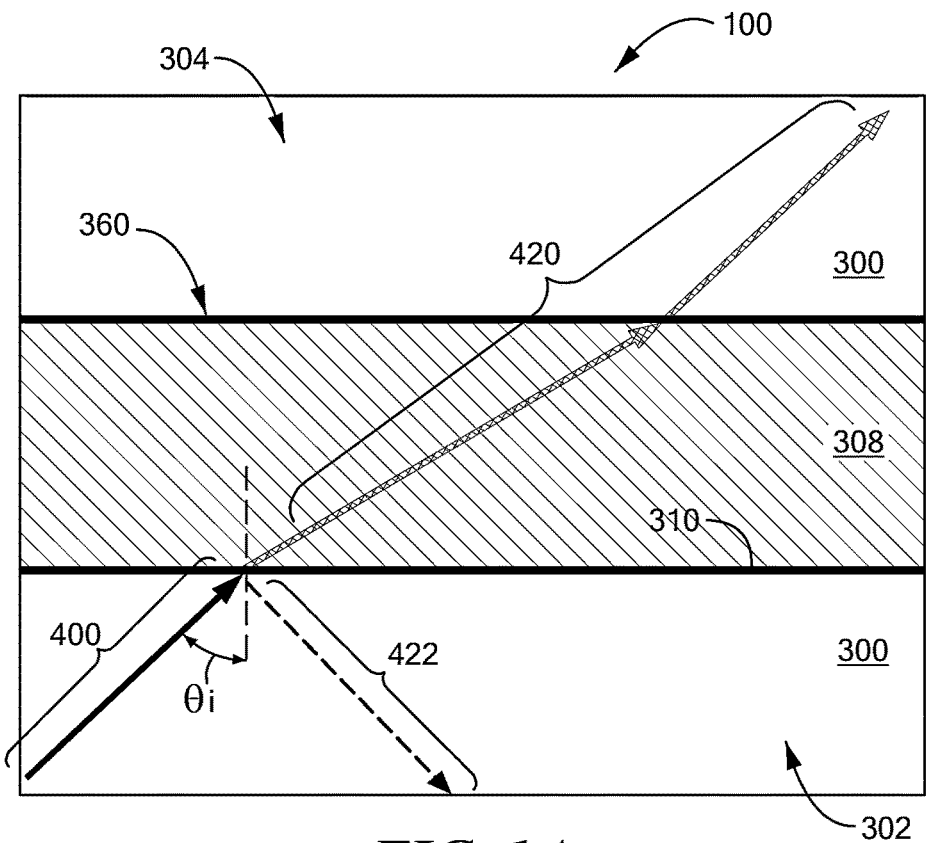
FIG. 1A depicts a block diagram representation of a portion of an optical sensor with an incident light primarily refracted, in accordance with an embodiment.

One skilled in the art will understand that the drawings, further described herein below, are for illustration purposes only. It will be appreciated that for simplicity and clarity of illustration, elements shown in the figures have not necessarily been drawn to scale. For example, the dimensions or scale of some of the elements may be exaggerated relative to other elements for clarity. Further, where considered appropriate, reference numerals may be repeated among the figures to indicate corresponding or analogous elements, or analogous elements may not be repetitively enumerated in all figures where it will be appreciated and understood that such enumeration where absent is inherently disclosed.

DETAILED DESCRIPTION

As used herein, the phrase "embodiment" means "embodiment disclosed and/or illustrated herein", which may not necessarily encompass a specific embodiment of an invention in accordance with the appended claims, but nonetheless is provided herein as being useful for a complete understanding of an invention in accordance with the appended claims.

Although the following detailed description contains many specifics for the purposes of illustration, anyone of ordinary skill in the art will appreciate that many variations and alterations to the following details are within the scope of the appended claims. For example, where described features may not be mutually exclusive of and with respect to other described features, such combinations of non-mutually exclusive features are considered to be inherently disclosed herein. Additionally, common features may be commonly illustrated in the various figures but may not be specifically enumerated in all figures for simplicity, but would be recognized by one skilled in the art as being an explicitly disclosed feature even though it may not be enumerated in a particular figure. Accordingly, the following example embodiments are set forth without any loss of generality to, and without imposing limitations upon, the claimed invention disclosed herein.

In an embodiment, a sensor and a disposable set is provided for detecting gas bubbles in a liquid-filled flow channel or small amounts of liquid in an otherwise dry channel. In an embodiment, the disposable set includes a fluid flow channel, and a holder for the fluid flow channel. In an embodiment, the holder and the fluid flow channel is an integrally formed monolithic construct. In another embodiment, the holder and the fluid flow channel are separable from each other. One of a fundamental principle applied herein operates on the principle of Total Internal Reflection, TIR. TIR is a phenomenon where a beam of light, when it reaches the interface of two mediums, is completely reflected into the original medium it traveled through. TIR occurs when the angle of incidence of the light is greater than a certain limiting angle, called the critical angle. The critical angle is a function of the refractive indices of the two materials involved, with the refractive index being an intrinsic property of a particular material.

The refractive index of many gases (including air) is approximately 1.00 while the refractive index of many commonly used liquids is between approximately 1.3 and 1.5. Due to this significant difference in the refractive index between gases and liquids, a sensor can be designed that allows a beam of light from a laser, diode, or other light source, to travel through a flow channel and a liquid contained in it in a predictable predetermined path. In this same configuration, if a gas bubble intersects the path of the light, the sensor and flow channel are designed in such a way, as disclosed herein, that the light will reflect via TIR in a different direction. An optical receiver placed in the light path when liquid is present or when gas is present or both is used to determine whether liquid or gas is present in the fluid flow channel.

Stated alternatively, the critical angle principle in the field of optics, and as applied herein, is based on the phenomenon where refraction of a light beam occurs at a medium1-medium2 interface, where medium1 is a known optically transparent medium having an index of refraction n1, and medium2 is a known liquid having an index of refraction n2 (where n1>n2), and where the angle of incidence from medium1 toward medium2 is less than the critical angle (at the medium-liquid interface); and where reflection of the light beam occurs at the medium1-medium2 interface, where medium1 is the known optically transparent medium having the index of refraction n1, and medium2 is now a known gas having an index of refraction n2 (where n1>n2), and where the angle of incidence from medium1 toward medium2 is greater than the critical angle (at the medium-gas interface). The critical angle is defined by Snell's Law, which states:

$$\text{Sin } \theta_1 / \text{Sin } \theta_2 = n_2/n_1;$$

where n1 and n2 are the aforementioned respective indices of refraction, θ1 is the angle of incidence of the light beam in medium1 (relative to a normal line at the medium-liquid interface), and θ2 is the angle of refraction of the light beam in medium2 (relative to a normal line at the medium-gas interface). The critical angle θ1 is determined by setting θ2=90-degrees (maximum angle of refraction), applying known values for n1 and n2, and solving for θ1. For example: (1) for n1=1.49 (acrylic), n2=1.33 (water), θ2=90-degrees (set to maximum angle of refraction), then θ1 (critical angle)=63.2-degrees; (2) for n1=1.49 (acrylic), n2=1 (air), θ2=90-degrees (set to maximum angle of refraction), then θ1 (critical angle)=42.2-degrees. Total internal reflection occurs where the angle of incidence is greater than the critical angle. As such, and for the aforementioned example, if the angle of incidence is set between 42.2-degrees and 63.2-degrees, then refraction will occur where medium1 is acrylic and medium2 is water, and reflection will occur where medium1 is acrylic and medium2 is air. As will be appreciated by the foregoing, if medium1 is fixed, and medium2 varies between water and air, then detection of this variance may be achieved by selective use a medium1 material and an appropriate selection for an angle of incidence. As will also be appreciated by the foregoing example, other angles of incidence may be employed by selective use of different materials for medium1 and medium2.

In view of the foregoing, an embodiment provides, as shown and described by the various figures and accompanying text, an optical bubble sensor that employs the critical angle principle to provide an arrangement where the light beam undergoes refraction at a medium-liquid interface, and undergoes reflection at a medium-gas interface, by setting the angle of incidence of the light beam directed toward the medium-liquid/gas interface so that refraction occurs in the presence of liquid at the medium-liquid/gas interface, and reflection occurs in the present of gas at the medium-liquid/gas interface. As used herein, the term "medium" as it is used in the phrase "medium-liquid/gas" refers to the material of medium1 used for transmitting the incident light beam emitted from an optical transmitter toward the medium-liquid/gas interface (on a first side of the medium-liquid/gas interface), where medium1 may be an acrylic for example, and the term "liquid/gas" as it is used in the phrase "medium-liquid/gas" refers to the material of medium2 present on a second side of the medium-liquid/gas interface opposing the first side, which may be a liquid, or a gas, or a mixture of a liquid and a gas (e.g., gas bubbles). In an embodiment, the material of medium2 is present in, and may also be transitory through, a flow channel that may be part of the aforementioned disposable set.

The flow channel may be made of any material that is optically transmissive (transparent or translucent) such as polycarbonate, acrylic, or glass. The interface between the sensor and the flow channel may be any optically transparent material suitable for a purpose disclosed herein. In one embodiment, the interface between the sensor and the disposable set can simply be an air gap (i.e. no coupling material is needed) as long as the angles at the interface of the sensor and the disposable set are designed in such a way that there is no TIR at the sensor-air gap interface or the air gap-disposable set interface when the appropriate optical conditions are present.

Figure 1B:
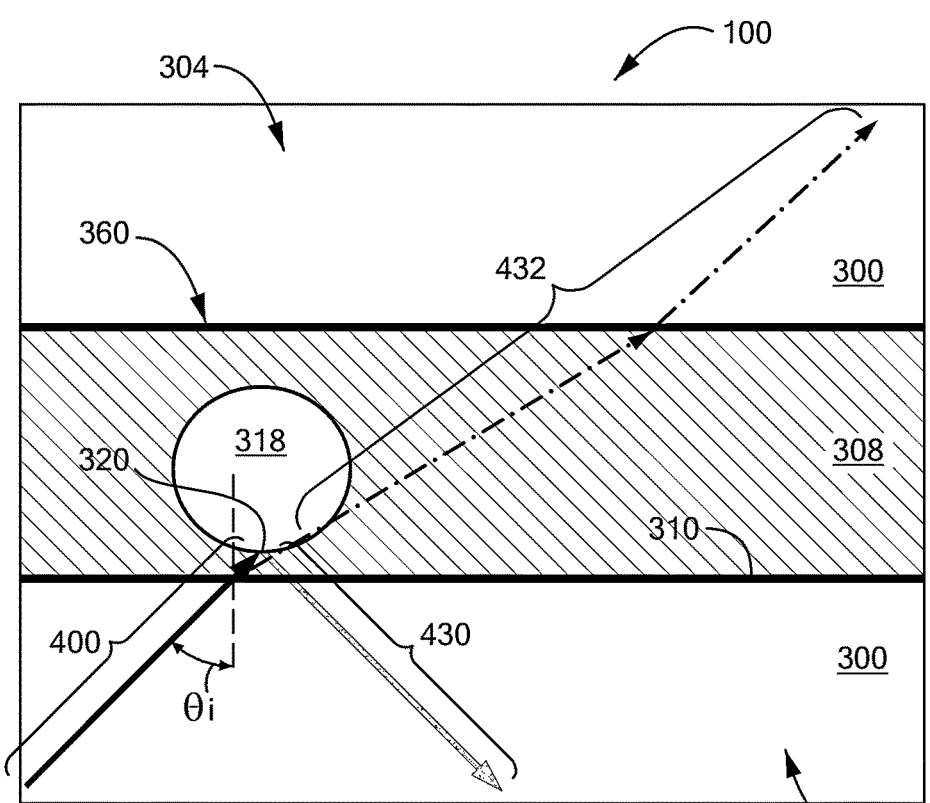
FIG. 1B depicts a block diagram representation of the optical sensor portion of FIG. 1A with an incident light primarily reflected, in accordance with an embodiment.
Figure 1C:
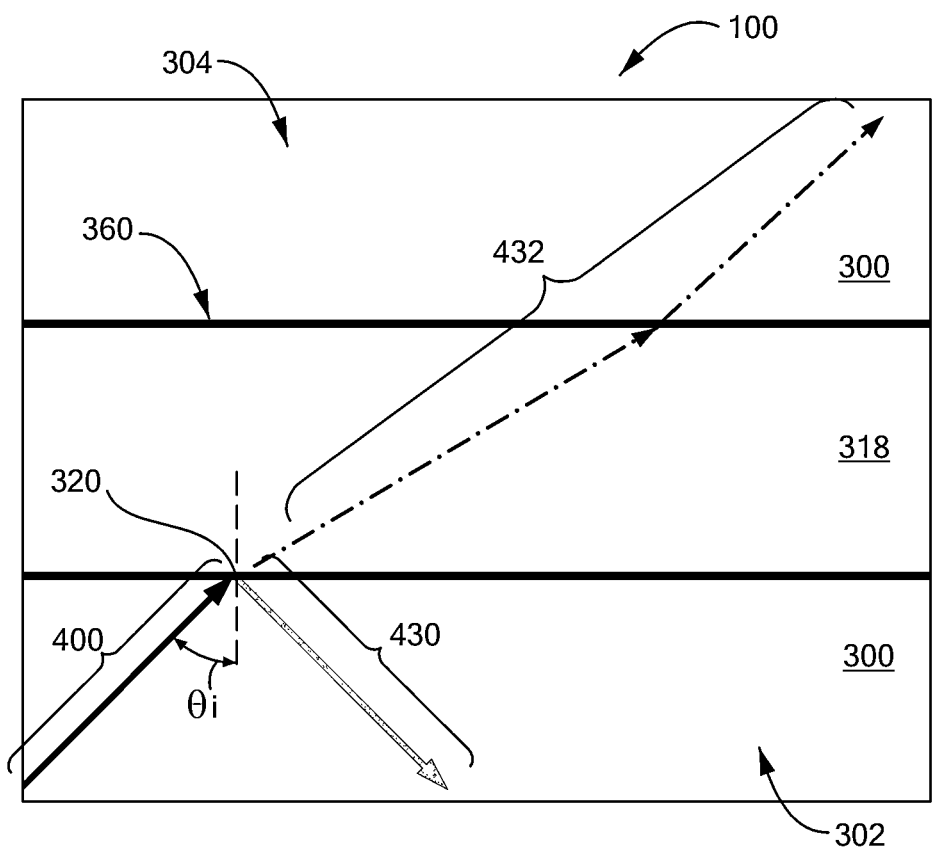
FIG. 1C depicts a block diagram representation of the optical sensor portion of FIG. 1A with an incident light primarily reflected alternative to that of FIG. 1B, in accordance with an embodiment.

Reference is first made to FIGS. 1A, 1B, and 1C, collectively, which illustrate the foregoing description of the critical angle principle with an eye toward an embodiment of an optical bubble sensor 100 as disclosed herein.

In FIG. 1A, a wettable component 300 is illustrated having a first side 302 and a second side 304 with a fluid flow channel 360 disposed therebetween. In an embodiment, the wettable component 300 includes a housing 350 (best seen with reference to FIGS. 2A-2B) having the fluid flow channel 360 disposed therein. An incident light beam 400 is depicted being emitted from an optical transmitter 220 (best seen with reference to FIGS. 2A-2B) that is directed towards and encounters a liquid interface 310 between the fluid flow channel 360 and a liquid 308 within the fluid flow channel 360 at an angle of incidence θi. In the illustrated example of FIG. 1A, the angle of incidence θi is less than a first critical angle θ1cr, which is defined relative to the material of the wettable component 300 and the material of the liquid 308, resulting in refraction of the incident light 400. As used herein, the term "wettable component" refers to a component that would be typically dry prior to use, and would be typically wet or wetted, via fluid flow internal of the fluid flow channel 360, when in use.

In the presence of the liquid 308, such as water, saline fluid, or blood for example, substantially filling the fluid flow channel 360 of the wettable component 300, the angle of incidence θi is set such that the majority of the incident light 400 refracts at the liquid interface 310 between the fluid flow channel 360 and the liquid 308, and travels through the entirety of the fluid flow channel 360 from the first side 302 to the second side 304 of the fluid flow channel 360, the majority of the incident light 400 that refracts is herein referred to as the majority of the incident light refracted 420. As used herein, the majority of the incident light refracted 420 is defined as that portion of the incident light 400 that is received by a refractive receiver 242 (best seen with reference to FIGS. 2A-2B)), regardless of how many interfaces it may travel through from the optical transmitter 220 to the refractive receiver 242. The majority of the incident light refracted 420 has an optical intensity above a defined threshold (discussed further herein below).

Further in the presence of the liquid 308 substantially filling the fluid flow channel 360 of the wettable component 300, a minority portion of the incident light 400 reflects at the liquid interface 310 between the fluid flow channel 360 and the liquid 308 and does not travel through the entirety of the fluid flow channel 360, which is contemplated to result from imperfections at the liquid interface 310 that cause the optical interactions of the incident light 400 to deviate from theoretically ideal conditions. The feature of the minority portion of the incident light 400 that reflects is herein referred to as the minority portion of the incident light reflected 422, which in an embodiment travels from the wettable component 300 to a sensor portion 200 and is received by a reflective receiver 246 (best seen with reference to FIGS. 2A-2B)

As used herein, the phrase "substantially filling" means that the fluid flow channel 360 of the wettable component 300 has more of the liquid 308 than a gas 318 (best seen with reference to FIGS. 1A-1C) that is sufficient to cause a majority of the incident light 400 to refract at the subject interface 310, but does not preclude some of the incident light 400, the minority portion of the incident light 422, from being reflected at the same subject interface 310.

In FIG. 1B, the same wettable component 300 as that of FIG. 1A is illustrated. As depicted, the fluid flow channel 360 contains both the liquid 308 and the gas 318 (the gas 318 being depicted as a gas bubble). Similar to FIG. 1A, the incident light 400 emitted from the optical transmitter 220 and is directed towards and encounters the liquid interface 310, as described above. A difference between FIG. 1A and FIG. 1B is that the majority of the incident light refracted 420 here encounters a gas interface 320 between the fluid flow channel 360, or the liquid 308 in the fluid flow channel 360, and the gas 318 in the fluid flow channel 360, at an angle of incidence θi. In the illustrated example of FIG. 1B, the angle of incidence θi is greater than a second critical angle θ2cr, which is defined relative to the material of the wettable component 300 and the material of the gas 318, resulting in reflection of the incident light 400.

In the presence of the gas 318 in the fluid flow channel 360 of the wettable component 300, the majority of the incident light 400 reflects at the gas interface 320 and does not travel through the entirety of the fluid flow channel 360 from the first side 302 to the second side 304 of the fluid flow channel 360, the majority of the incident light 400 that reflects is herein referred to as the majority of the incident light reflected 430. As used herein, the majority of the incident light reflected 430 is defined as that portion of the incident light 400 that is received by the reflective receiver 246, regardless of how many interfaces it may travel through from the optical transmitter 220 to the reflective receiver 246. The majority of the incident light reflected 430 has an optical intensity above a defined threshold (discussed further herein below).

Further in the presence of the gas 318 in the fluid flow channel 360 of the wettable component 300, a minority portion of the incident light 400 refracts at the gas interface 320 between the fluid flow channel 360, or the liquid 308 in the fluid flow channel 360, and the gas 318, and travels through the entirety of the fluid flow channel 360 from the first side 302 to the second side 304 of the fluid flow channel 360, the minority portion of the incident light 400 that refracts is herein referred to as the minority portion of the incident light refracted 432, which in an embodiment travels from the wettable component 300 to the sensor portion 200 and is received by the refractive receiver 242. The occurrence of the minority portion of the incident light refracted 432 is contemplated to result from imperfections at the liquid interface 310 that cause the optical interactions of the incident light 400 to deviate from theoretically ideal conditions.

In FIG. 1C, the same wettable component 300 as that of FIGS. 1A and 1B is illustrated. As depicted, the fluid flow channel 360 is devoid of any of the liquid 308, and instead is filled with the gas 318. Similar to the scenario of FIG. 1B, the incident light 400 emitted from the optical transmitter 220 is directed towards and encounters a gas interface 320, same reference numeral used as the gas interface 320 discussed above due to the similarities in the optical conditions, between the first side 302 of the wettable component 300 and the fluid flow channel 360. Here, and similar to that of FIG. 1B, the angle of incidence θi of the incident light 400 relative to the gas interface 320 is greater than the second critical angle θ2cr, resulting in the majority of the incident light 400 being reflected at the gas interface 320 and not travelling through the entirety of the fluid flow channel 360 from the first side 302 to the second side 304 of the fluid flow channel 360.

Again similar to that of FIG. 1B, in the presence of the gas 318 (a bubble of gas 318 as depicted in FIG. 1B, or completely gas 318 as depicted in FIG. 1C) in the fluid flow channel 360 of the wettable component 300, a minority portion of the incident light 400 refracts at the gas interface 320 between the fluid flow channel 360, or the liquid 308 in the fluid flow channel 360, and the gas 318, and travels through the entirety of the fluid flow channel 360 from the first side 302 to the second side 304 of the fluid flow channel 360.

From the foregoing, it will be appreciated that an embodiment disclosed herein includes an arrangement where the optical transmitter 220 is configured, disposed, and arranged so as to direct the incident light 400 emitted from the optical transmitter 220 towards the fluid flow channel 360 of the wettable component 300 at an angle of incidence θi that is less than the first critical angle θ1cr, and is greater than the second critical angle θ2cr. Stated alternatively, the incident light 400 is directed towards the fluid flow channel 360 at an angle of incidence θi between the first critical angle θ1cr and the second critical angle θ2cr.

Figure 2A:
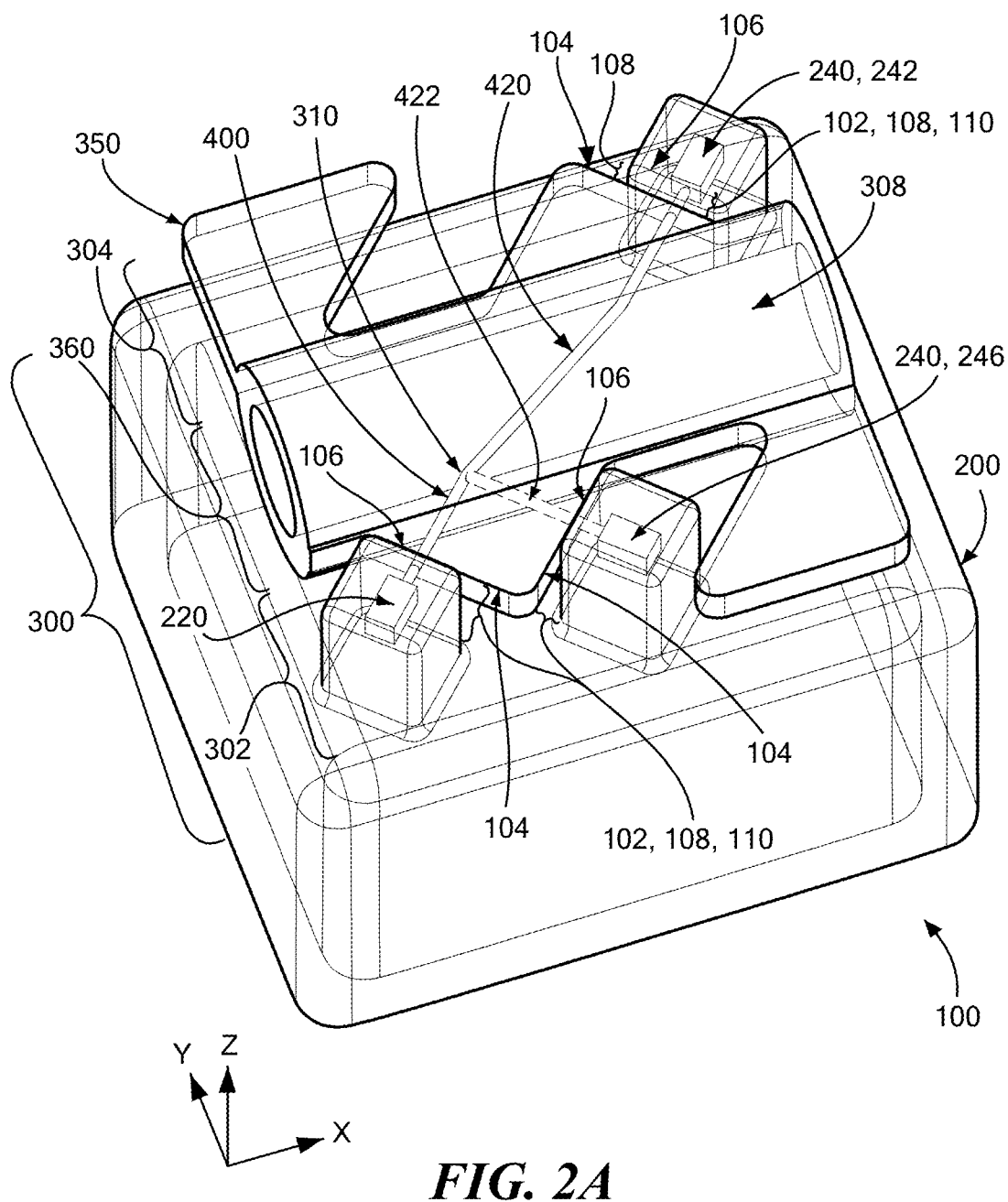
FIG. 2A depicts a transparent rotated isometric view of an optical sensor with an incident light primarily refracted, in accordance with an embodiment.
Figure 2B:
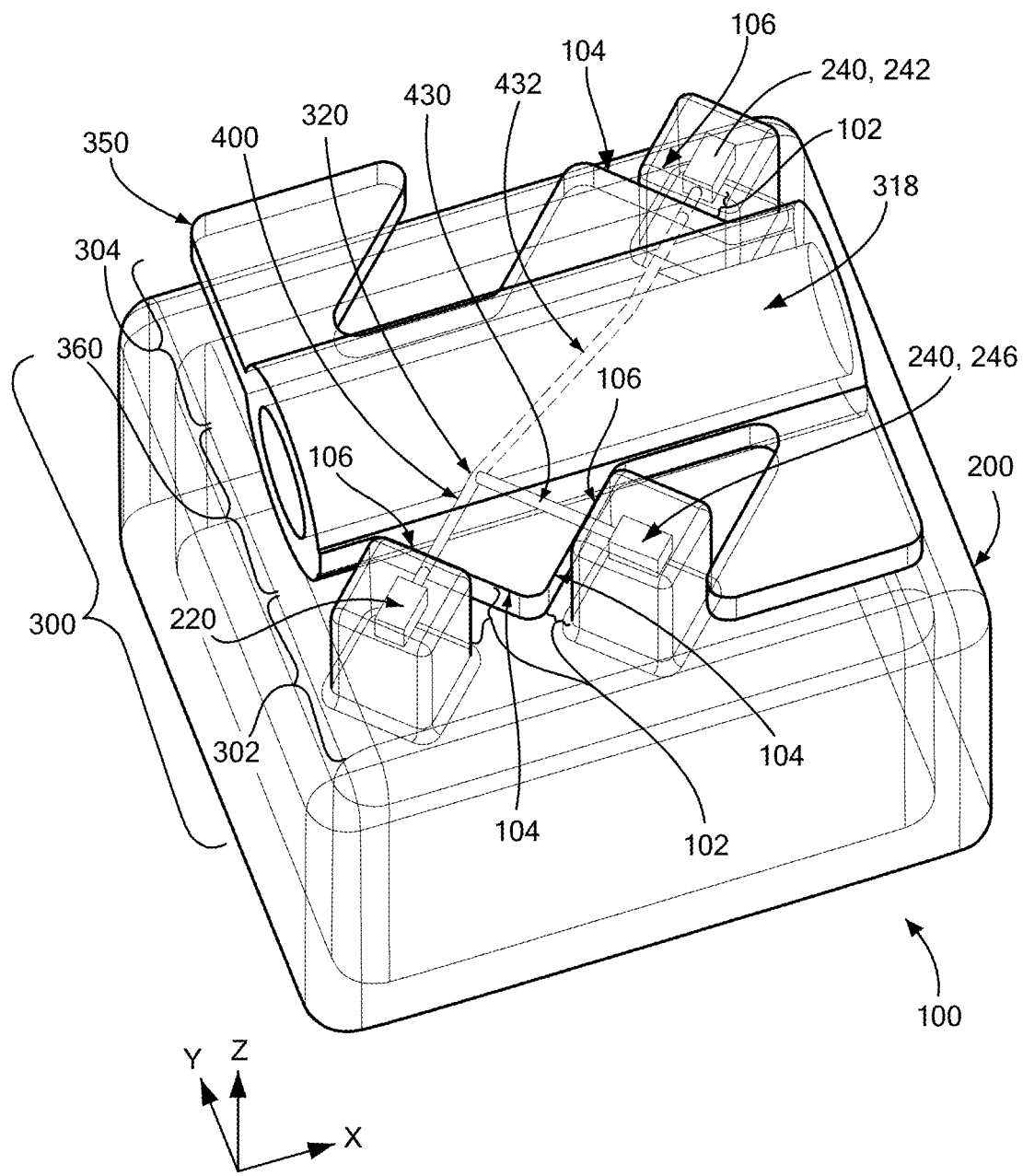
FIG. 2B depicts a transparent rotated isometric view of the optical sensor of FIG. 2A with an incident light primarily reflected, in accordance with an embodiment.

Reference is now made to FIGS. 2A and 2B collectively, and in combination with FIGS. 1A-1C, which further disclose an embodiment of the optical sensor 100 disclosed partially in connection with FIGS. 1A-1C, where FIG. 2A depicts an arrangement of the optical sensor 100 similar to that of FIG. 1A, in that the optical transmitter 220 and the reflective receiver 246 are disposed on the first side 302 of the fluid flow channel 360, the refractive receiver 242 is disposed on the second side 304 of the fluid flow channel 360, and the fluid flow channel 360 is substantially full of the liquid 308; and, where FIG. 2B depicts an arrangement of the optical sensor 100 similar to that of FIG. 1C, in that the optical transmitter 220 and the reflective receiver 246 are disposed on the first side 302 of the fluid flow channel 360, the refractive receiver 242 is disposed on the second side 304 of the fluid flow channel 360, and the fluid flow channel 360 is substantially full of the gas 318. As depicted, the optical sensor 100 has a sensor portion 200 having an optical transmitter 220 and at least one optical receiver 240, and is configured to couple to the wettable component 300 via at least one coupling interface 102. In an embodiment, the wettable component 300 is configured as the aforementioned disposable set, but in a particular embodiment may also be fixed relative to the sensor 200. As depicted, the wettable component 300 includes a housing 350 having the fluid flow channel 360. The at least one coupling interface 102 has at least one coupling surface 104 on the wettable component 300, and at least one coupling surface 106 on the sensor portion 200. In an embodiment at the at least one coupling interface 102, the corresponding at least one coupling surface 104 on the wettable component 300 and/or the corresponding at least one coupling surface 106 on the sensor portion 200 may have a space or gap 108 therebetween, which in an embodiment may be filled with a transmissive material 110, such as a gas, a liquid, or a solid, for material (best seen with reference to FIGS. 2A, 5A, and 5B). While the space/gap 108 and transmissive material 110 is illustratively depicted only in FIGS. 2A, 5A, and 5B, it will be appreciated that the scope of an embodiment disclosed herein, and a scope of the appended claims, is not so limited, and that such space/gap 108 and transmissive material 110 may also be applicable to the embodiments of 2B, 3A, 3B, 4A, 4B, 5A, and 5B, and fall within a scope of the appended claims. Examples of the transmissive material 110 include but are not limited to: air, optically clear silicone rubber, grease, oil, and water. The at least one optical receiver 240 includes a refractive receiver 242, a reflective receiver 246, or both the refractive receiver 242 and the reflective receiver 246, wherein the optical transmitter 220 is disposed and configured to emit the incident light 400. In an embodiment, the optical transmitter 220 and the at least one coupling interface 102 are disposed such that the incident light 400 emitted from the optical transmitter 220, when active, travels from the sensor portion 200 towards the wettable component 300 where a majority of the incident light 400 is directed towards the fluid flow channel 360 at an angle between the aforementioned first critical angle θ1cr and the aforementioned second critical angle θ2cr.

With respect to the foregoing, at least one of: the majority of the incident light refracted 420 (see FIG. 2A); and, the majority of the incident light reflected 430 (see FIG. 2B), travels from the wettable component 300 towards the sensor portion 200 and is received by the at least one optical receiver 240, wherein the at least one optical receiver 240 is disposed such that it intersects at least one of: the majority of incident light refracted 420; and, the majority of the incident light reflected 430; and, wherein at least one of: the amount of the majority of the incident light refracted 420 and received by the at least one optical receiver 240; and, the amount of the majority of the incident light reflected 430 and received by the at least one optical receiver 240, is used to determine if there is liquid 308 or gas 306 in the fluid flow channel 360. In an embodiment, a micro-processing circuit responsive to machine executable instructions which when executed by the micro-processing circuit is used to determine if there is liquid 308 or gas 306 in the fluid flow channel 360. To assist in such determination, a predefined threshold is employed to distinguish between a majority of the incident light refracted 420, and a majority of the incident light reflected 430.

While FIGS. 2A and 2B depict the refractive receiver 242 and the reflective receiver 246, it will be appreciated that both receivers may not be needed for a particular use or application. As such, an embodiment may be employed absent one of the reflective receiver 246 or the refractive receiver 242, but not absent both, and still provide functionality consistent with the disclosure herein, and consistent with a scope of the appended claims. As such, FIGS. 2A and 2B can be interpreted to disclose an embodiment of the optical sensor 100 having just the refractive receiver 242, having just the reflective receiver 246, or having both the refractive receiver 242 and the reflective receiver 246.

Figure 3A:
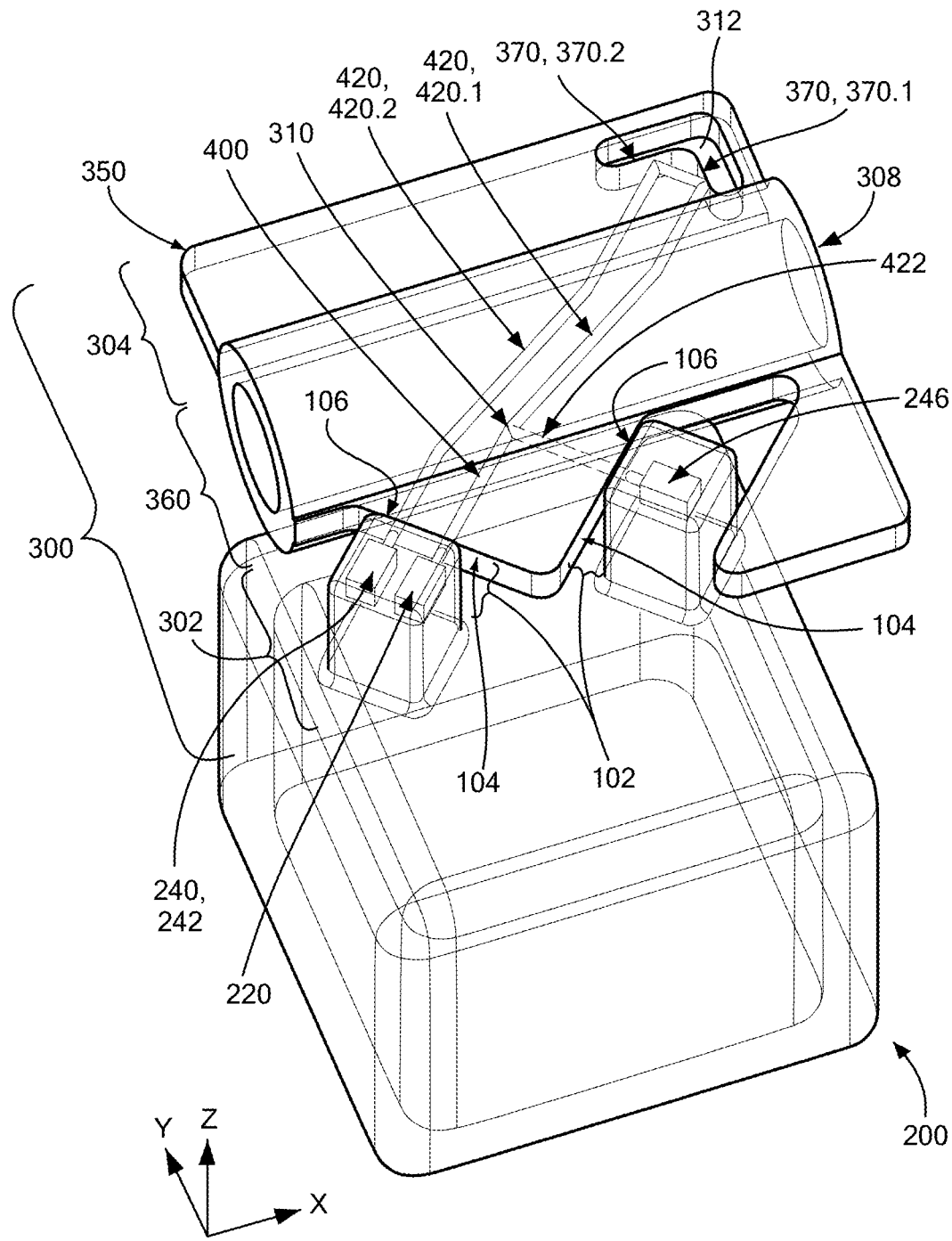
FIG. 3A depicts a transparent rotated isometric view of an optical sensor alternative to that of FIG. 2A with an incident light primarily refracted, in accordance with an embodiment.
Figure 3B:
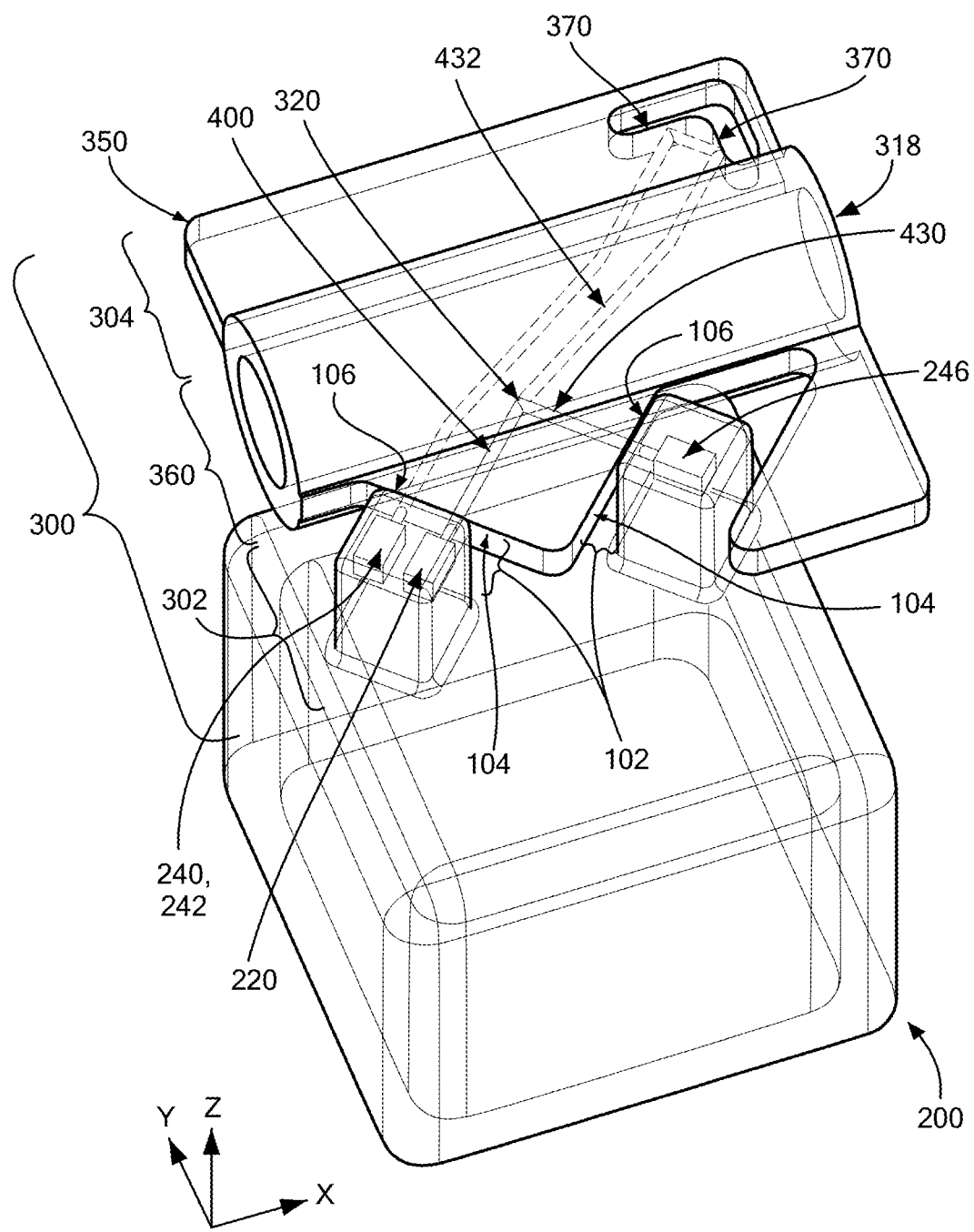
FIG. 3B depicts a transparent rotated isometric view of the optical sensor of FIG. 3A with an incident light primarily reflected, in accordance with an embodiment.
Figure 4A:
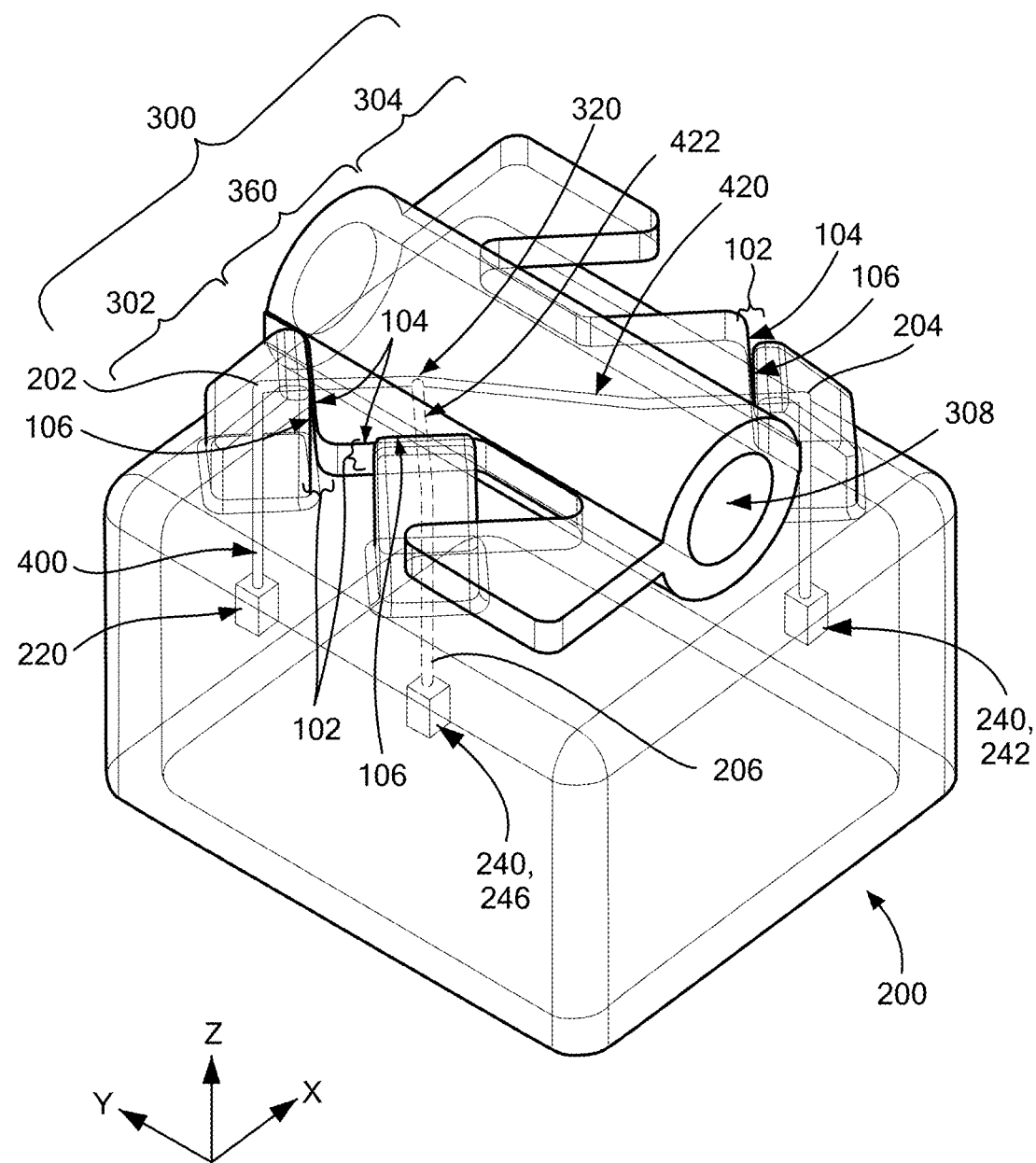
FIG. 4A depicts a transparent rotated isometric view of another optical sensor alternative to that of FIG. 2A with an incident light primarily refracted, in accordance with an embodiment.
Figure 4B:
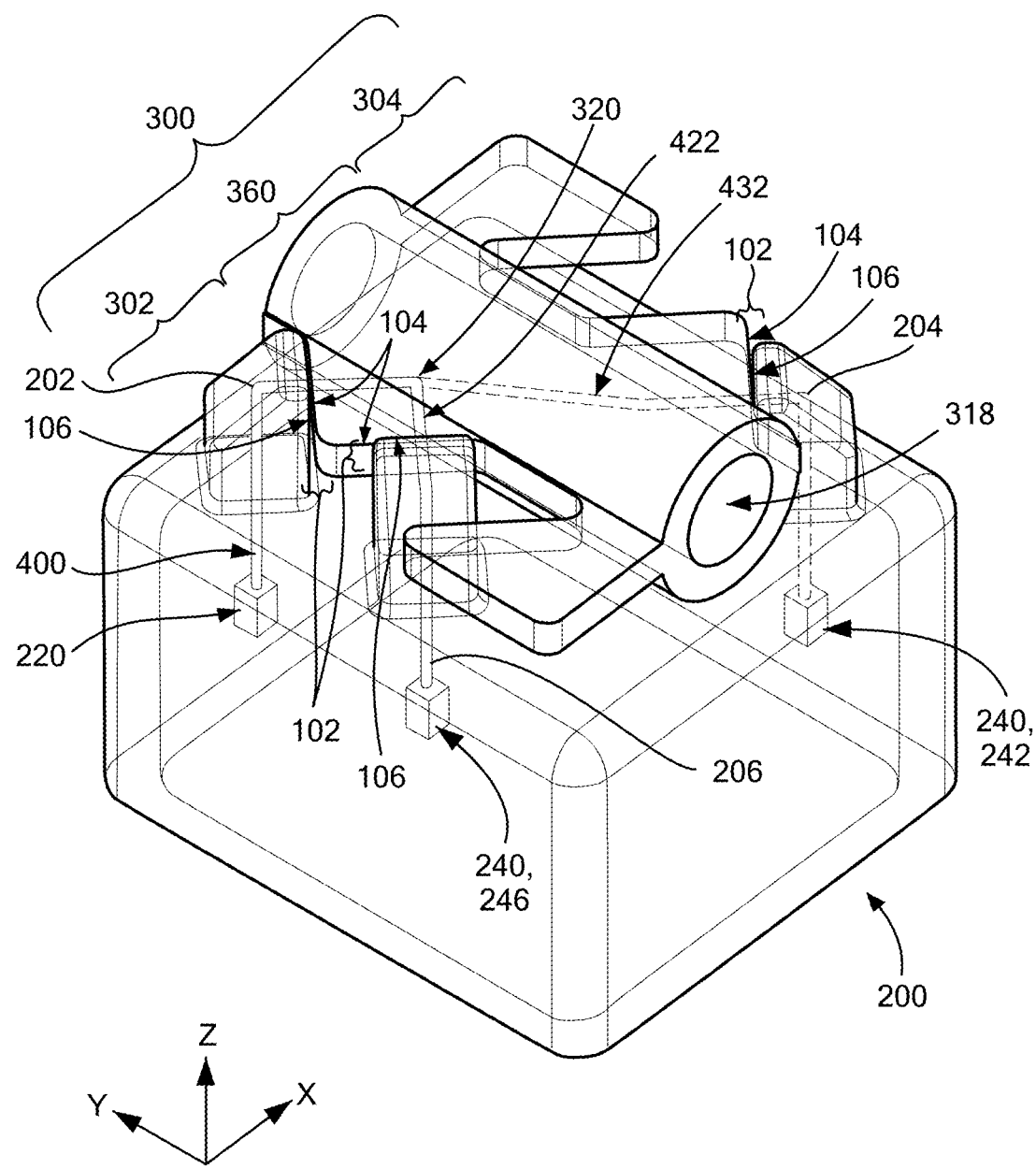
FIG. 4B depicts a transparent rotated isometric view of the optical sensor of FIG. 4A with an incident light primarily reflected, in accordance with an embodiment.
Figure 5A:
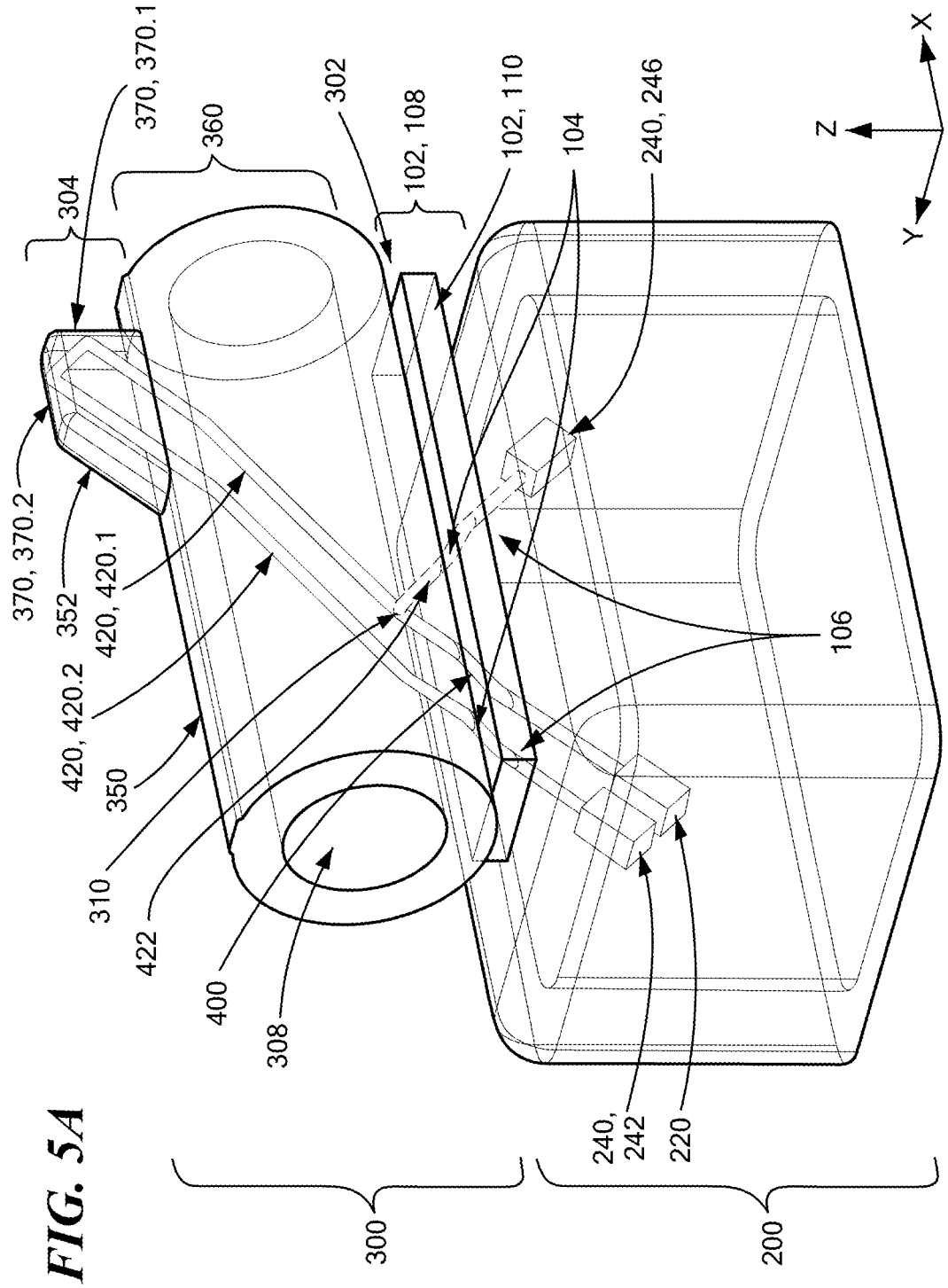
FIG. 5A depicts a transparent rotated isometric view of another optical sensor alternative to that of FIG. 2A with an incident light primarily refracted, in accordance with an embodiment.
Figure 5B:
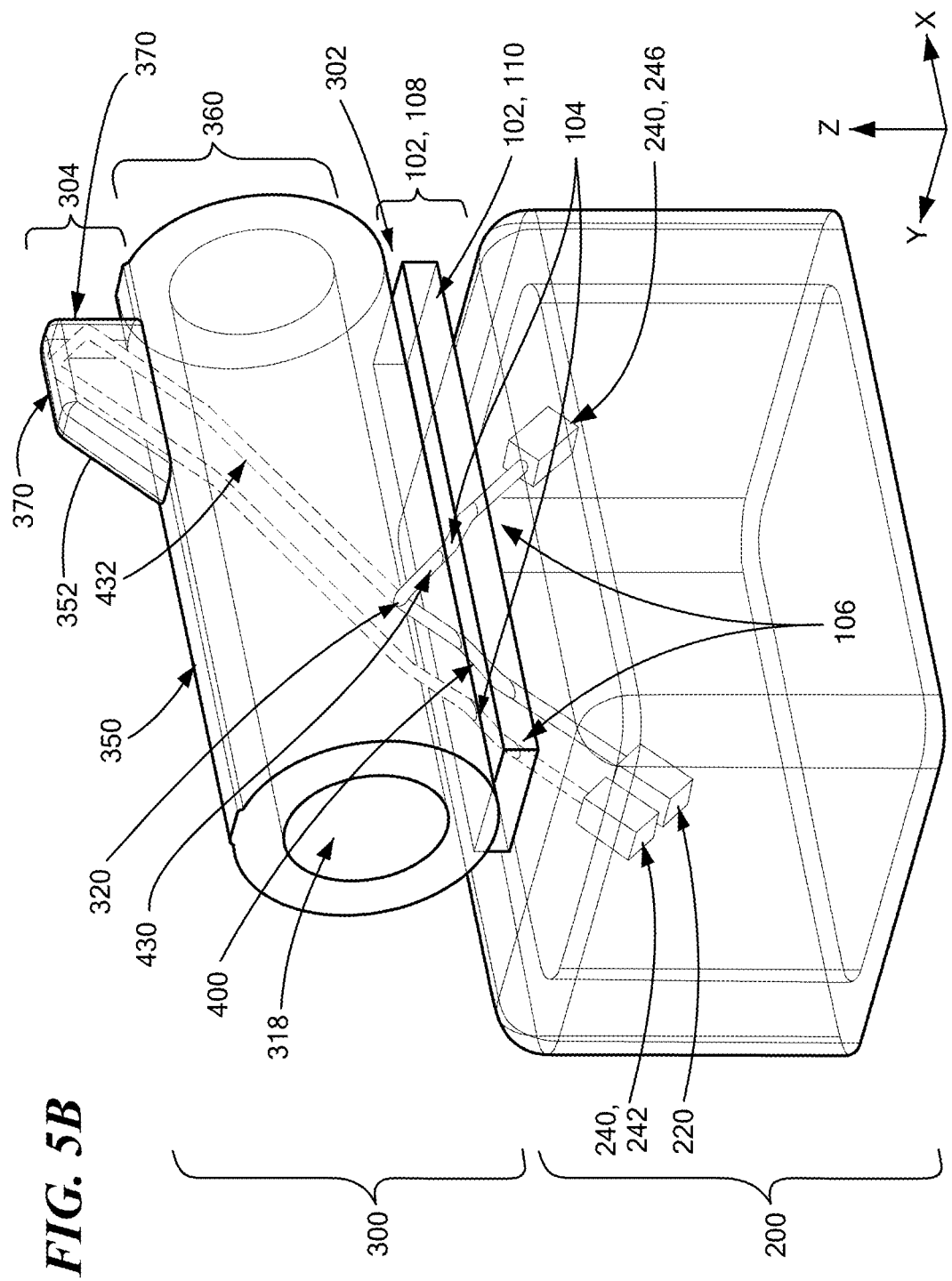
FIG. 5B depicts a transparent rotated isometric view of the optical sensor of FIG. 5A with an incident light primarily reflected, in accordance with an embodiment.

Reference is now made to FIGS. 3A, 3B, 4A, 4B, 5A, and 5B, which depict variations of the structural arrangement of the optical features depicted in FIGS. 1A, 1C 2A, and 2B, where like elements are numbered alike. For example, and in comparison to: FIGS. 2A and 2B wherein the optical transmitter 220 is disposed on the first side 302 of the fluid flow channel 360, and the refractive receiver 242 is disposed on the second side 304 of the fluid flow channel 360; FIGS. 3A and 3B depict an arrangement wherein the optical transmitter 220 and the refractive receiver 242 are both disposed on the first side 302 of the fluid flow channel 360, but with reflective surfaces 370 disposed on the second side 304 of the fluid flow channel 360 (discussed further below); FIGS. 4A and 4B depict an arrangement wherein the optical transmitter 220 is disposed on the first side 302 of the fluid flow channel 360 and the refractive receiver 242 is disposed on the second side 304 of the fluid flow channel 360, but where the incident light 400, the majority of the incident light refracted 420, the minority portion of the incident light reflected 422, the majority of the incident light reflected 430, and the minority portion of the incident light refracted 432, propagate along light paths that differ from those of FIGS. 2A and 2B, which will be discussed further below; and, FIGS. 5A and 5B depict an arrangement similar to that depicted in FIGS. 3A and 3B, but wherein the housing 350 of the wettable component 300 is oriented differently, a coupling interface 102 is provided (discussed further herein below), and reflective surfaces 370 on the second side 304 of the fluid flow channel 360 are configured differently (discussed further herein below).

Specific variations of FIGS. 3A, 3B, 4A, 4B, 5A, and 5B, relative to FIGS. 2A and 2B will now be discussed individually.

Reference is now made to FIGS. 3A and 3B. As noted above, FIGS. 3A and 3B depict an arrangement wherein the optical transmitter 220 and the refractive receiver 242 are both disposed on the first side 302 of the fluid flow channel 360, but with reflective surfaces 370 formed in the housing 350 on the second side 304 of the fluid flow channel 360. In an embodiment and as depicted, the reflective surfaces 370 of FIGS. 3A and 3B include first and second reflective surfaces 370.1 and 370.2 that are formed by removal of the material of the second side 304 of the fluid flow channel 360 that forms a void 312 in the second side 304 to create a mediumA-mediumB interface (mediumA being the material of the second side 304, and medium being air) that forms a 90-degree angle between the first and second reflective surfaces 370.1, 370.2 such that the majority of the incident light refracted 420 on an outgoing path 420.1, is reflected and returned back towards the first side 302 on a parallel incoming path 420.2 that is parallel to the outgoing path 420.1, where it is received by the refractive receiver 242. In another embodiment, the reflective surfaces 370 may include a reflective material, such as a metallic coating for example, rather than being reliant on just TIR. While FIGS. 3A and 3B depict the second side 304 of the fluid flow channel 360 being formed by an elongated planer projection that extends the entire length of the wettable component 300, it will be appreciate that a scope of the appended claims is not limited by such an arrangement, as one skilled in the art would readily be able to envision other arrangements that would function equivalently, such as for example a projection that extends off of the second side 304 of the fluid flow channel 360 only in the vicinity of the reflective surfaces 370 depicted, and not along an entire length of the wettable component 300 (see FIGS. 5A and 5B for example). Any and all embodiments that fall within a scope of the appended claims are contemplated and considered to be inherently disclosed herein.

Reference is now made to FIGS. 4A and 4B. As noted above, FIGS. 4A and 4B depict an arrangement wherein the optical transmitter 220 is disposed on the first side 302 of the fluid flow channel 360 and the refractive receiver 242 is disposed on the second side 304 of the fluid flow channel 360, but where the incident light 400, the majority of the incident light refracted 420, the minority portion of the incident light reflected 422, the majority of the incident light reflected 430, and the minority portion of the incident light refracted 432, propagate along light paths that differ from those of FIGS. 2A and 2B. For example, and relative to the x-y-z orthogonal coordinate system depicted and in the presence of the liquid 308, the optical transmitter 220 is disposed and oriented such that the incident light 400 first travels in a positive z-direction in a plane parallel with the z-axis, is reflected 90-degrees by a first reflective surface 202 in the sensor portion 200, then travels in an x-y plane through the fluid flow channel 360, then is reflected 90-degrees by a second reflective surface 204 in the sensor portion 200 to travel in a negative z-direction in a plane parallel with the z-axis, and is received by the refractive receiver 242. A similar positioning of the reflective receiver 246 is made such that the minority of the incident light reflected 422 undergoes a 90-degree reflection at a third reflective surface 206 in the sensor portion.

Reference is now made to FIGS. 5A and 5B. As noted above, FIGS. 5A and 5B depict an arrangement similar to that depicted in FIGS. 3A and 3B, but wherein the housing 350 of the wettable component 300 is oriented with an projection 352 extending upwards in line with the majority of the incident light refracted 420 to provide sufficient material on the second side 304 of the wettable components 300 to create a mediumA-mediumB interface (mediumA being the material of the second side 304, and medium being air) that forms a 90-degree angle between the first and second reflective surfaces 370.1, 370.2 (collectively 370) such that the majority of the incident light refracted 420 on an outgoing path 420.1, is reflected and returned back towards the first side 302 on a parallel incoming path 420.2 that is parallel to the outgoing path 420.1, where it is received by the refractive receiver 242. In addition, FIGS. 5A and 5B depict a space or gap 108 between the sensor 200 and the wettable component 300 at the coupling interface 102 where a transmissive material 110 is optionally positioned, which may be useful in avoiding contaminants from migrating into the space/gap 108 that could negatively impact the optical performance of the optical bubble sensor 100 if the space/gap 108 was just occupied by air.

While certain combinations of individual features have been described and illustrated herein, it will be appreciated that these certain combinations of features are for illustration purposes only and that any combination of any of such individual features may be employed in accordance with an embodiment, whether or not such combination is explicitly illustrated, and consistent with the disclosure herein. Any and all such combinations of features as disclosed herein are contemplated herein, are considered to be within the understanding of one skilled in the art when considering the application as a whole, and are considered to be within the scope of the invention disclosed herein, as long as they fall within the scope of the invention defined by the appended claims, in a manner that would be understood by one skilled in the art.

While an invention has been described herein with reference to example embodiments, it will be understood by those skilled in the art that various changes may be made and equivalents may be substituted for elements thereof without departing from the scope of the claims. Many modifications may be made to adapt a particular situation or material to the teachings of the invention without departing from the essential scope thereof. Therefore, it is intended that the invention not be limited to the particular embodiment or embodiments disclosed herein as the best or only mode contemplated for carrying out this invention, but that the invention will include all embodiments falling within the scope of the appended claims. In the drawings and the description, there have been disclosed example embodiments and, although specific terms and/or dimensions may have been employed, they are unless otherwise stated used in a generic, exemplary and/or descriptive sense only and not for purposes of limitation, the scope of the claims therefore not being so limited. The use of the terms first, second, etc. do not denote any order or importance, but rather the terms first, second, etc. are used to distinguish one element from another. The use of the terms a, an, etc. do not denote a limitation of quantity, but rather denote the presence of at least one of the referenced item. The term "comprising" as used herein does not exclude the possible inclusion of one or more additional features. And, any background information provided herein is provided to reveal information believed by the applicant to be of possible relevance to the invention disclosed herein. No admission is necessarily intended, nor should be construed, that any of such background information constitutes prior art against an embodiment of the invention disclosed herein.

In view of all of the foregoing, it will be appreciated that various aspects of an embodiment are disclosed herein, which are in accordance with, but not limited to, at least the following aspects and/or combinations of aspects.

Aspect 1: An optical sensor, having: a sensor portion having an optical transmitter and at least one optical receiver, the sensor portion being configured to couple to a wettable component at least one coupling interface, the wettable component having a housing with a fluid flow channel, the at least one coupling interface having of at least one coupling surface on the wettable component and at least one coupling surface on the sensor portion, the at least one optical receiver having a refractive receiver, a reflective receiver, or both the refractive receiver and the reflective receiver, wherein the optical transmitter is disposed and configured to emit an incident light; wherein the optical transmitter and the at least one coupling interface are disposed such that the incident light emitted from the optical transmitter, when active, travels from the sensor portion to the wettable component where a majority of the incident light is directed towards the fluid flow channel at an angle between a first critical angle and a second critical angle, the first critical angle being defined relative to the wettable component and a liquid, and the second critical angle being defined relative to the wettable component and a gas; wherein in the presence of a liquid substantially filling the fluid flow channel of the wettable component, the majority of the incident light refracts at a liquid interface between the fluid flow channel and the liquid and travels through the entirety of the fluid flow channel; wherein in the presence of a gas in the fluid flow channel of the wettable component, the majority of the incident light reflects at a gas interface between the fluid flow channel, or the liquid in the fluid flow channel, and the gas, and does not travel through the entirety of the fluid flow channel; wherein at least one of: the majority of the incident light refracted; and, the majority of the incident light reflected, travels from the wettable component to the sensor portion and is received by the at least one optical receiver; wherein the at least one optical receiver is disposed such that it intersects at least one of: the majority of incident light refracted; and, the majority of the incident light reflected; and, wherein at least one of: the amount of the majority of the incident light refracted and received by the at least one optical receiver; and, the amount of the majority of the incident light reflected and received by the at least one optical receiver, is used to determine if there is liquid or gas in the fluid flow channel.

Aspect 2: The sensor of Aspect 1, wherein: in the presence of a liquid substantially filling the fluid flow channel of the wettable component, a minority portion of the incident light reflects at the liquid interface between the fluid flow channel and the liquid and does not travel through the entirety of the fluid flow channel.

Aspect 3: The sensor of Aspect 1, wherein: in the presence of a gas in the fluid flow channel of the wettable component, a minority portion of the incident light refracts at a gas interface between the fluid flow channel, or the liquid in the fluid flow channel, and the gas, and travels through the entirety of the fluid flow channel.

Aspect 4: The sensor of Aspect 2, wherein: the minority portion of the incident light reflected travels from the wettable component to the sensor portion, and is received by the reflective receiver.

Aspect 5: The sensor of Aspect 3, wherein: the minority portion of the incident light refracted travels from the wettable component to the sensor portion and is received by the refractive receiver.

Aspect 6: The sensor of any one of Aspects 1 to 5, wherein: the at least one optical receiver includes the refractive receiver and the reflective receiver.

Aspect 7: The sensor of any one of Aspects 1 to 6, wherein: the at least one optical receiver is the refractive receiver.

Aspect 8: The sensor of any one of Aspects 1 to 7, wherein: the at least one optical receiver is the reflective receiver.

Aspect 9: The sensor of Aspect 6, wherein: in the presence of liquid substantially filling the fluid flow channel of the wettable component, the majority of the incident light refracted is received by the refractive receiver, and the minority portion of the incident light reflected is received by the reflective receiver.

Aspect 10. The sensor of Aspect 6, wherein: in the presence of gas within the fluid flow channel of the wettable component, the majority of the incident light reflected is received by the reflective receiver, and the minority portion of the incident light refracted is received by the refractive receiver.

Aspect 11: The sensor of Aspect 7, wherein: in the presence of liquid substantially filling the fluid flow channel of the wettable component, the majority of the incident light refracted is received by the refractive receiver.

Aspect 12: The sensor of Aspect 7, wherein: in the presence of gas within the fluid flow channel of the wettable component, the minority portion of the incident light refracted is received by the refractive receiver.

Aspect 13: The sensor of Aspect 8, wherein: in the presence of liquid substantially filling the fluid flow channel of the wettable component, the minority portion of the incident light reflected is received by the reflective receiver.

Aspect 14: The sensor of Aspect 8, wherein: in the presence of gas within the fluid flow channel of the wettable component, the majority of the incident light reflected is received by the reflective receiver.

Aspect 15: The sensor of any one of Aspects 1 to 14, wherein: the at least one coupling surface on the wettable component and the at least one coupling surface on the sensor portion includes a space therebetween, wherein the space is filled with a transmissive material.

Aspect 16: The sensor of Aspect 15, wherein: the transmissive material includes a gas.

Aspect 17: The sensor of Aspect 15, wherein: the transmissive material includes a liquid.

Aspect 18: The sensor of Aspect 15, wherein: the transmissive material includes a solid.

The invention claimed is:

1. An optical sensor, comprising:
a sensor portion comprising an optical transmitter and at least one optical receiver, the sensor portion being configured to couple to a wettable component at at least one coupling interface, the wettable component comprising a housing with a fluid flow channel, the at least one coupling interface comprising of at least one coupling surface on the wettable component and at least one coupling surface on the sensor portion, the at least one optical receiver comprising a refractive receiver, a reflective receiver, or both the refractive receiver and the reflective receiver, wherein the optical transmitter is disposed and configured to emit an incident light;
wherein the optical transmitter and the at least one coupling interface are disposed such that the incident light emitted from the optical transmitter, when active, travels from the sensor portion to the wettable component where a majority of the incident light is directed towards the fluid flow channel at an angle between a first critical angle and a second critical angle, the first critical angle being defined relative to the wettable component and a liquid, and the second critical angle being defined relative to the wettable component and a gas;
wherein in the presence of a liquid substantially filling the fluid flow channel of the wettable component, the majority of the incident light refracts at a liquid interface between the fluid flow channel and the liquid and travels through the entirety of the fluid flow channel;
wherein in the presence of a gas in the fluid flow channel of the wettable component, the majority of the incident light reflects at a gas interface between the fluid flow channel, or the liquid in the fluid flow channel, and the gas, and does not travel through the entirety of the fluid flow channel;
wherein at least one of: the majority of the incident light refracted; and, the majority of the incident light reflected, travels from the wettable component to the sensor portion and is received by the at least one optical receiver;
wherein the at least one optical receiver is disposed such that it intersects at least one of: the majority of incident light refracted; and, the majority of the incident light reflected; and
wherein at least one of: the amount of the majority of the incident light refracted and received by the at least one optical receiver; and, the amount of the majority of the incident light reflected and received by the at least one optical receiver, is used to determine if there is liquid or gas in the fluid flow channel.

2. The sensor of claim 1, wherein:
in the presence of a liquid substantially filling the fluid flow channel of the wettable component, a minority portion of the incident light reflects at the liquid interface between the fluid flow channel and the liquid and does not travel through the entirety of the fluid flow channel.

3. The sensor of claim 2, wherein:
the minority portion of the incident light reflected travels from the wettable component to the sensor portion, and is received by the reflective receiver.

4. The sensor of claim 1, wherein:
in the presence of a gas in the fluid flow channel of the wettable component, a minority portion of the incident light refracts at a gas interface between the fluid flow channel, or the liquid in the fluid flow channel, and the gas, and travels through the entirety of the fluid flow channel.

5. The sensor of claim 4, wherein:
the minority portion of the incident light refracted travels from the wettable component to the sensor portion and is received by the refractive receiver.

6. The sensor of claim 1, wherein:
the at least one optical receiver comprises the refractive receiver and the reflective receiver.

7. The sensor of claim 6, wherein:
in the presence of liquid substantially filling the fluid flow channel of the wettable component, the majority of the incident light refracted is received by the refractive receiver, and a minority portion of the incident light reflected is received by the reflective receiver.

8. The sensor of claim 6, wherein:
in the presence of gas within the fluid flow channel of the wettable component, the majority of the incident light reflected is received by the reflective receiver, and a minority portion of the incident light refracted is received by the refractive receiver.

9. The sensor of claim 1, wherein:
the at least one optical receiver is the refractive receiver.

10. The sensor of claim 9, wherein:
in the presence of liquid substantially filling the fluid flow channel of the wettable component, the majority of the incident light refracted is received by the refractive receiver.

11. The sensor of claim 9, wherein:
in the presence of gas within the fluid flow channel of the wettable component, a minority portion of the incident light refracted is received by the refractive receiver.

12. The sensor of claim 1, wherein:
the at least one optical receiver is the reflective receiver.

13. The sensor of claim 12, wherein:
in the presence of liquid substantially filling the fluid flow channel of the wettable component, a minority portion of the incident light reflected is received by the reflective receiver.

14. The sensor of claim 12, wherein:
in the presence of gas within the fluid flow channel of the wettable component, the majority of the incident light reflected is received by the reflective receiver.

15. The sensor of claim 1, wherein:
the at least one coupling surface on the wettable component and the at least one coupling surface on the sensor portion comprises a space therebetween, wherein the space is filled with a transmissive material.

16. The sensor of claim 15, wherein:
the transmissive material comprises a gas.

17. The sensor of claim 15, wherein:
the transmissive material comprises a liquid.

18. The sensor of claim 15, wherein:
the transmissive material comprises a solid.

* * * * *